US009968381B2

(12) United States Patent
Thalgott et al.

(10) Patent No.: US 9,968,381 B2
(45) Date of Patent: May 15, 2018

(54) TRANSLAMINAR INTERSPINOUS STABILIZATION SYSTEM

(71) Applicant: Paradigm Spine, LLC, New York, NY (US)

(72) Inventors: John S. Thalgott, Las Vegas, NV (US); David T. Stinson, Woodinville, WA (US); Troy D. Drewry, Memphis, TN (US)

(73) Assignee: PARADIGM SPINE, LLC, New York, NY (US)

( * ) Notice: Subject to any disclaimer, the term of this patent is extended or adjusted under 35 U.S.C. 154(b) by 0 days. days.

(21) Appl. No.: 15/185,821

(22) Filed: Jun. 17, 2016

(65) Prior Publication Data

US 2016/0296258 A1    Oct. 13, 2016

Related U.S. Application Data

(63) Continuation of application No. 13/366,790, filed on Feb. 6, 2012, now Pat. No. 9,370,382.
(Continued)

(51) Int. Cl.
*A61B 17/70* (2006.01)
*A61F 2/28* (2006.01)
*A61B 17/68* (2006.01)

(52) U.S. Cl.
CPC ...... *A61B 17/7067* (2013.01); *A61B 17/7062* (2013.01); *A61F 2/2846* (2013.01); *A61B 2017/681* (2013.01); *A61F 2002/2839* (2013.01)

(58) Field of Classification Search
CPC ............ A61B 17/7062; A61B 17/7067; A61B 17/7068; A61B 17/7071
(Continued)

(56) References Cited

U.S. PATENT DOCUMENTS 5,645,599 A   7/1997   Samani
6,974,478 B2  12/2005  Reiley et al.
(Continued)

FOREIGN PATENT DOCUMENTS

CN    101332116 A    12/2008
CN    101785696 A    7/2010
(Continued)

OTHER PUBLICATIONS

Extended European Search Report dated Sep. 9, 2016, European Application No. 16167090, pp. 1-8.
(Continued)

*Primary Examiner* — Ellen C Hammond
*Assistant Examiner* — Christina Negrellirodriguez
(74) *Attorney, Agent, or Firm* — Farber LLC

(57) ABSTRACT

A translaminar, interspinous stabilization system is provided. The system may comprise an implantable device for placement between two adjacent vertebrae. The device may comprise an inferior section, a superior section, and a flexible midsection extending therebetween and configured to seat against the lamina between the adjacent vertebrae. A pair of lateral plates may extend from at least one of the inferior section and superior section for engaging a laminar surface of one of the vertebra. Each of the lateral plates includes an aperture for receiving a bone screw therethrough. Also provided is a bone screw for placement through at least one lateral plate for securing the device to the laminar surface of one of the vertebra.

14 Claims, 10 Drawing Sheets

Related U.S. Application Data

(60) Provisional application No. 61/439,918, filed on Feb. 6, 2011.

(58) Field of Classification Search
USPC .......................................... 606/246–249, 279
See application file for complete search history.

(56) References Cited

U.S. PATENT DOCUMENTS

| | | | |
|---|---|---|---|
| 7,011,685 | B2 | 3/2006 | Arnin et al. |
| 7,537,613 | B2 | 5/2009 | Arnin et al. |
| 7,811,322 | B2 | 10/2010 | Arnin et al. |
| 7,811,330 | B2 | 10/2010 | Arnin et al. |
| 7,837,711 | B2 | 11/2010 | Bruneau et al. |
| 7,850,733 | B2 | 12/2010 | Baynham et al. |
| 7,922,750 | B2 | 4/2011 | Trautwein et al. |
| 8,002,801 | B2 | 8/2011 | Carl et al. |
| 8,529,626 | B2 * | 9/2013 | Seme ............. A61B 17/7062 606/249 |
| 2003/0040746 | A1 | 2/2003 | Mitchell et al. |
| 2004/0158246 | A1 | 8/2004 | Assaker et al. |
| 2004/0162558 | A1 | 8/2004 | Hegde et al. |
| 2005/0267579 | A1 | 12/2005 | Reiley et al. |
| 2006/0229620 | A1 | 10/2006 | Rothman et al. |
| 2006/0241601 | A1 | 10/2006 | Trautwein et al. |
| 2006/0282077 | A1 | 12/2006 | Labrom et al. |
| 2008/0045954 | A1 | 2/2008 | Reiley et al. |
| 2008/0097440 | A1 | 4/2008 | Reiley et al. |
| 2008/0097446 | A1 | 4/2008 | Reiley et al. |
| 2008/0177263 | A1 | 7/2008 | Freedman et al. |
| 2008/0228225 | A1 | 9/2008 | Trautwein et al. |
| 2009/0005819 | A1 | 1/2009 | Ben-Mokhtar et al. |
| 2009/0149885 | A1 | 6/2009 | Durward et al. |
| 2009/0270919 | A1 * | 10/2009 | Dos Reis, Jr. ..... A61B 17/7062 606/249 |
| 2010/0131008 | A1 | 5/2010 | Overes et al. |
| 2010/0191287 | A1 | 7/2010 | Bucci |
| 2011/0029020 | A1 | 2/2011 | Gordon et al. |
| 2011/0040330 | A1 * | 2/2011 | Sheffer ............. A61B 17/7062 606/249 |
| 2011/0106163 | A1 | 5/2011 | Hochschuler et al. |
| 2011/0144693 | A1 | 6/2011 | Black |
| 2011/0190819 | A1 | 8/2011 | Trautwein et al. |
| 2011/0218572 | A1 | 9/2011 | Lechmann et al. |

FOREIGN PATENT DOCUMENTS

| | | |
|---|---|---|
| FR | 2722980 A1 | 2/1996 |
| TW | M381378 U | 6/2010 |
| WO | 03/007829 A1 | 1/2003 |
| WO | 2008067452 | 6/2008 |
| WO | 2011109197 | 9/2011 |

OTHER PUBLICATIONS

Author Unknown, Patent Examination Report No. 1 dated Aug. 19, 2015, Australian Application No. 2012211951, pp. 1-3.

Author Unknown, International Search Report dated May 7, 2012, PCT Application No. PCT/US2012/023946.

Author Unknown, Chinese Office Action dated Feb. 28, 2017, Chinese Application No. 201280016732.9, filed Sep. 30, 2013, pp. 1-8 (including english translation).

Chinese Office Action dated Jun. 23, 2017 in corresponding CN Application No. 201280016732.9, 16 pages.

* cited by examiner

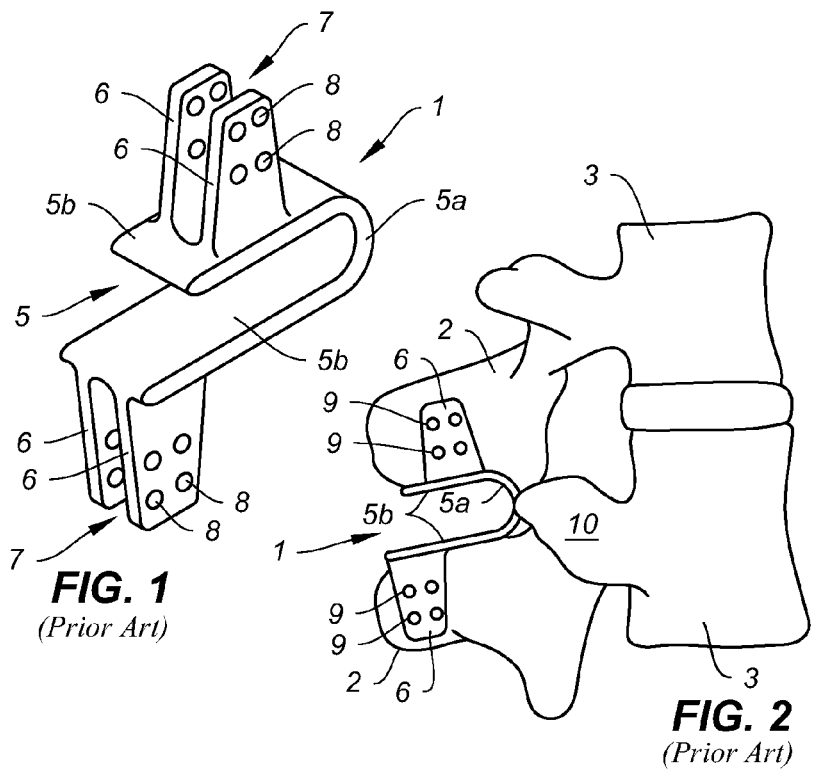
FIG. 1
*(Prior Art)*
FIG. 2
*(Prior Art)*
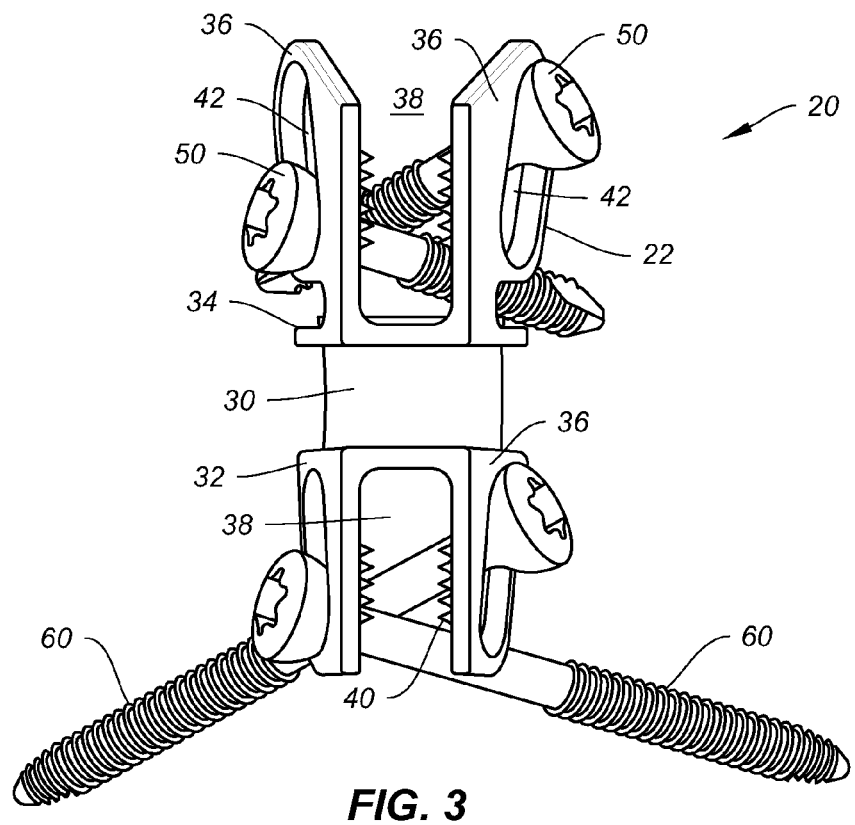
FIG. 3

TRANSLAMINAR INTERSPINOUS STABILIZATION SYSTEM

CROSS-REFERENCE TO RELATED APPLICATIONS

This application is a continuation of U.S. application Ser. No. 13/366,790 filed Feb. 6, 2012, (now allowed), which application claims benefit of U.S. Provisional Application No. 61/439,918 filed Feb. 6, 2011, both of which are entitled "Translaminar Interspinous Stabilization System", the contents of which are incorporated herein by reference in their entirety.

FIELD

The present disclosure relates to devices and methods for treating spine instability, including translaminar interspinous stabilization systems and methods of using such systems for segmental stabilization of adjacent vertebrae.

BACKGROUND

Spinal instability is often attributed to undesirable excessive motion between vertebrae and can cause significant pain and morbidity. The instability may result from a number of causes, including abnormalities of the vertebrae, the intervertebral discs, the facet joints, and connective tissue around the spine. These abnormalities may arise from diseases, disorders or defects of the spine from trauma or bone degradation, such as osteoarthritis, or degenerative disc disease. When the spine becomes unstable, the vertebral column becomes misaligned and may produce micromotion between adjacent vertebrae. Vertebral misalignment and micromotion may result in wear to the vertebral bone surfaces and ultimately generate severe pain. These conditions are often chronic and create progressive problems for the sufferer.

Known treatments for spinal instability can include long-term medical management or surgery. Medical management is generally directed at controlling the symptoms, such as pain reduction, rather than correcting the underlying problem. For some patients, this may require chronic use of pain medications, which may alter patient mental state or cause other negative side effects. Surgical treatment typically includes decompression procedures to restore normal disc height, realign the column, and alleviate the pain.

Recently, a variety of interspinous stabilization devices have become available. These devices are typically implanted between the spinous processes of two or more adjacent vertebrae. By stabilizing the spinous processes in this way, significant stress may be taken off the intervertebral discs to prevent disease progression or to improve conditions such as spinal stenosis. In addition, vertebral motion may be controlled without severely altering the anatomy of the spine.

These devices, along with other interspinous stabilization systems, can be secured between adjacent spinous processes using a number of different mechanisms. For example, such devices can include sharp barbs or other surface projections that engage the bony surface of a spinous process. In addition, flexible ligaments or sutures can be placed around the implants and adjacent bone. In some cases, the devices may be rigidly attached to the spinous process using a bone screw or other suitable bone anchor to prevent the interspinous device from migrating or slipping out of position.

It may be desirable in some situations, such as where the spinous process is damaged, weakened, brittle or insufficient in size to serve as a bearing surface, to provide an interspinous stabilization device that can be anchored translaminarly. It is further desirable to provide an interspinous stabilization system that can be configured to provide either dynamic or rigid stability to the affected vertebral segment of the spinal column. For instance, it would be desirable to provide such a system whereby the dynamic stability allows for controlled motion of the adjacent vertebrae being affected. It would be even more desirable to provide the same system having the ability to allow for rigid, fusion-promoting securement if so desired or needed. Further still, it would be desirable to provide a system that can provide the option of either dynamic or rigid stability at different levels of the vertebral segment, while also allowing for multi-level vertebral stabilization.

SUMMARY

The present disclosure describes translaminar interspinous stabilization systems and methods of using these systems to treat spinal instability conditions. The systems may include an interspinous, interlaminar stabilization device configured for interlaminar placement between the spinous processes of adjacent vertebrae and secured to the lamina using bone screws placed translaminarly. Also provided are methods for using such systems.

One aspect of the disclosure relates to an implantable translaminar, interspinous stabilization system. The system may comprise an implantable device for placement between two adjacent vertebrae. The device may comprise an inferior section, a superior section, and a flexible midsection extending therebetween. The device is configured to seat against the lamina between the adjacent vertebrae. A pair of lateral plates may extend from the inferior section and superior section for engaging a laminar surface of one of the vertebra. Each of the lateral plates includes an aperture for receiving a bone fastener therethrough. The system may also comprise a first bone fastener for placement through one of the pair of lateral plates and a second bone fastener for placement through another one of the pair of lateral plates for securing the device to the laminar surface of the one of the vertebra.

A second aspect of the present disclosure relates to an implantable interspinous, interlaminar stabilization system. The system can comprise an implantable device for placement between two adjacent vertebrae. The device may comprise an inferior section, a superior section, and a flexible midsection extending therebetween and configured to seat against the lamina of the vertebrae, and a pair of lateral plates for engaging a laminar surface of one of the vertebra. Each of the lateral plates may include an aperture for receiving a bone fastener. At least one screw may be provided for placement through at least one lateral plate for securing the device to the laminar surface of one of the vertebra.

A third aspect of the present disclosure relates to a method of segmental stabilization of a spine. The method may comprise selecting a vertebral level to be treated and then positioning an implantable device between two spinous processes of two vertebrae of the selected vertebral level. The implantable device may comprise an inferior section, a superior section, and a flexible midsection extending therebetween configured to seat against the lamina between the adjacent vertebrae. The implant may further include a pair of lateral plates extending from one of the inferior or superior sections, each of the lateral plates including an aperture for receiving a bone fastener therethrough and being configured to engage a laminar surface of one of the vertebrae. The implantable device can be secured by placing a bone fastener through one of the pair of lateral plates, securing the device to the laminar surface of one of the vertebra.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 1 illustrates a perspective view of an interspinous, interlaminar vertebral stabilization device of the prior art.

FIG. 2 illustrates a side view of the prior art device of FIG. 1 in situ.

FIG. 3 illustrates a front perspective view of a translaminar interspinous stabilization system of the present disclosure.

Figure 4A:
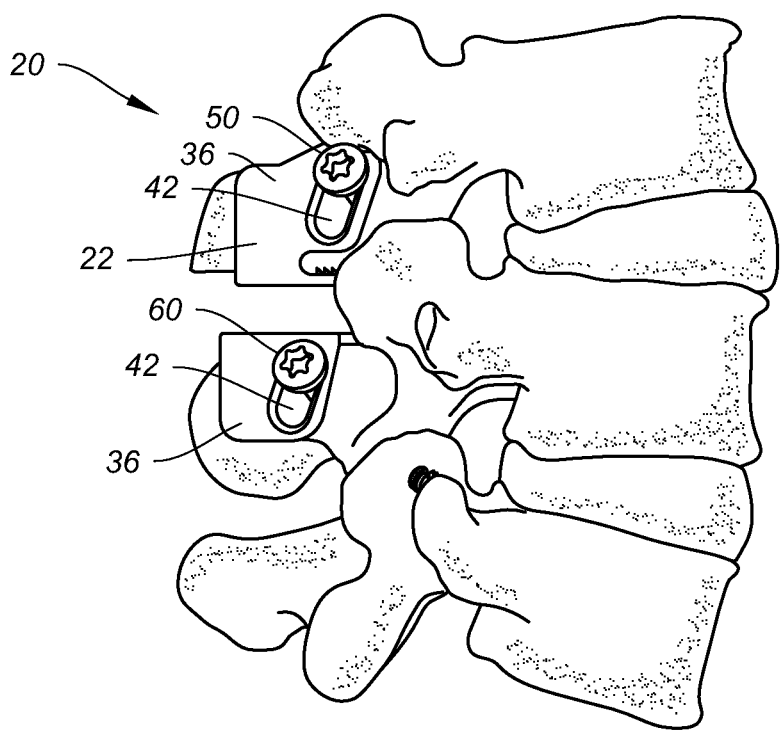
FIG. 4A illustrates a side view of the system of FIG. 3 in situ.

It is to be understood that both the foregoing general description and the following detailed description are exemplary and explanatory only, and are not restrictive of the disclosure, as claimed. Additional features of the disclosure will be set forth in part in the description which follows or may be learned by practice of the disclosure. The features of the disclosure will be realized and attained by means of the elements and combinations particularly pointed out in the appended claims.

DESCRIPTION OF THE EMBODIMENTS

FIGS. 1 and 2 show a conventional implantable interlaminar-interspinous vertebral implant 1 of the kind disclosed, for example, in U.S. Pat. No. 5,645,599 entitled "Interspinal Vertebral Implant" to Samani. The implant 1 may have a body 5, a central portion 5a, and two branches 5b in between. Brackets 6 extend from each of the two branches 5b and form stirrups 7 for receiving spinous processes of adjacent vertebrae 3 having articular processes 10 as shown. Holes 8 may be provided for receiving bone screws 9 or spikes for securing the implant 1 to the vertebrae 3.

FIG. 3 shows a translaminar interspinous vertebral stabilization system 20 of the present disclosure for stabilizing adjacent vertebrae. In one embodiment, the system 20 comprises an implantable, interlaminar-interspinous device 22 configured for placement between the spinous processes of adjacent vertebrae. The system 20 can include one or more fixation elements for securing the device 22 to the lamina of the adjacent vertebrae. In one embodiment, the fixation elements can rigidly fix the device with respect to the vertebrae, thereby limiting movement at a selected vertebral level and promoting fusion at that level. In another embodiment, the type of fixation elements may be varied to provide varying degrees of fixation strength. The system could, for instance, allow for a combination of dynamic stabilization of one vertebra and rigid stabilization of an adjacent vertebra at different levels of the spine.

As shown, the implantable device 22 may be formed as a spacer body. The device, or spacer body 22 may have various shapes and thicknesses, and can be produced from a variety of different materials alone or in combination. In one embodiment, the spacer body 22 may include a midsection 30 extending between an inferior section 32 and a superior section 34, as shown in FIG. 3. When implanted in a patient, the superior section 34 is configured to contact a portion of a first spinous process, while the inferior section 32 is configured to contact a portion of a second, adjacent spinous process. The spacer body 22 may be configured to be flexible and/or bendable. For example, the spacer body may comprise an extendable and/or compressible midsection 30. The midsection 30 can act as a flexible hinge, allowing the superior section 34 and inferior section 32 to move relative to each other, such as away from or towards one another. In one embodiment, the midsection 30, inferior section 32, and superior section 34 may together form a substantially U-shaped spacer body, as shown. The U-shaped spacer body enables the implantable device 22 to be positioned, or fitted, interlaminarly after implantation, thereby enhancing the stabilization of the adjacent vertebrae.

Figure 4B:
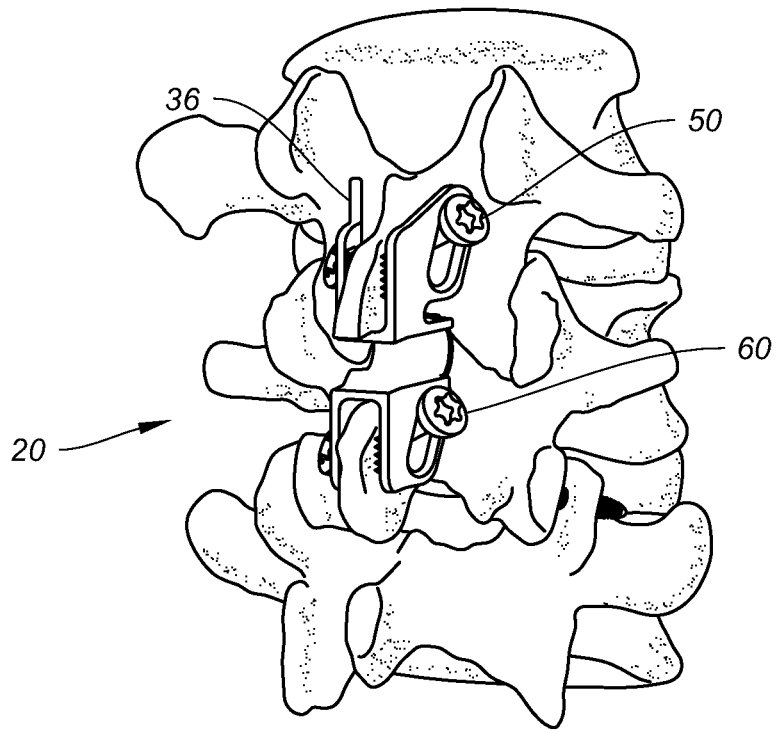
FIG. 4B illustrates a perspective view of the implanted system of FIG. 4A.
Figure 4C:
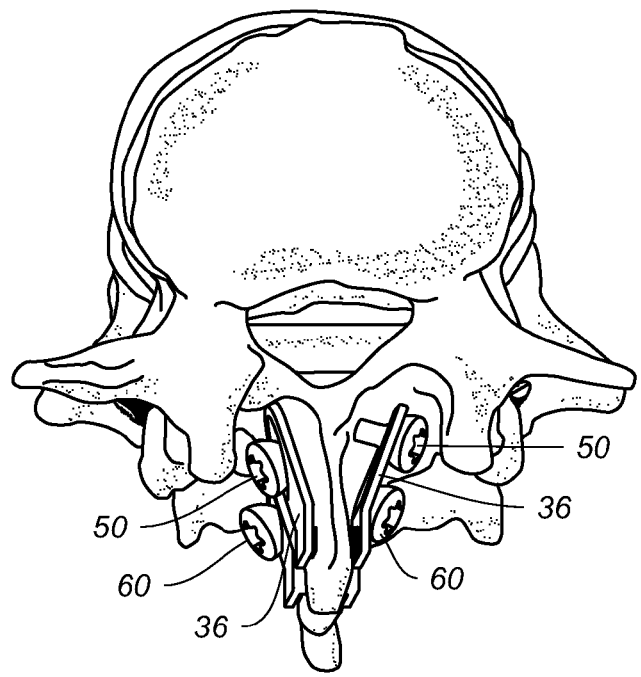
FIG. 4C illustrates a top-down view of the implanted system of FIG. 4A.

To engage the spinous processes of adjacent vertebrae, the spacer body 22 may be provided with a pair of lateral walls or brackets 36 that extend from the inferior and superior sections 32, 34, as shown in FIG. 3. Each of the pair of lateral walls 36 defines a stirrup 38 for receiving a spinous process. As further shown in FIGS. 4A-4C, the lateral walls 36 are configured with plate-like wings or extensions that extend beyond the spinous process and towards the lamina, and conform to the contours of the patient's anatomy. These walls 36 or plates may extend over a sizeable amount of lamina, as shown in FIGS. 4A and 4B. The walls 36 are shaped and sized to provide contact with the laminar surface around each respective spinous process, as further shown in FIG. 4C. As previously mentioned, providing an interspinous stabilization device 22 that can be securely anchored to the lamina may be desirable such as where the spinous process is damaged, weakened, brittle or insufficient in size to serve as a bearing surface.

In some embodiments, the lateral walls or plates 36 may be adjustable with respect to the spacer body 22. For example, the lateral walls 36 may be formed of a malleable material such that, after implantation, the surgeon may compress the lateral walls 36 together to reduce the gap between the lateral walls 36, thereby securely fixing the spacer body 22 to a spinous process located therein or an adjacent laminar surface. In addition, the lateral walls 36 may be spread apart to facilitate insertion. The lateral walls 36 may be compressed or spread apart, for example, using surgical pliers or forceps.

Each of the lateral walls or brackets 36 may include an aperture 42 for receiving a fixation element, such as, a bone fastener to fix the brackets 36 to the lamina. Such fastening elements can ensure that the brackets 36 lie flat and/or securely against the lamina in order to allow rigid fixation to the vertebrae. The aperture 42 can encompass a range of sizes and shapes. For example, the aperture 42 may be formed as an elongated slot as shown in FIGS. 3 and 4A. The apertures 42 of the inferior and superior sections 32, 34 may be staggered along a longitudinal axis, further shown in FIG. 4A. This feature allows a plurality of the implantable devices 22 to be stacked, or implanted, along the spinal column. Also contemplated is the use of the systems of the present disclosure with other implantable interlaminar-interspinous devices such as the ones described earlier. These other implantable interlaminar-interspinous devices could be stacked on top or below the systems presently described.

FIG. 3 illustrates one embodiment of the system 20 of the present disclosure in which a combination of dynamic stabilization and rigid stabilization can be achieved with the same device 22. In the system shown in FIG. 3, a different pair of fixation elements, or bone screws 50, 60 can be utilized. The pair of bone screws 50 extending through the top plates by way of apertures 42 is shorter in length than the pair of bone screws 60 extending through the bottom plates by way of apertures 42. By using different lengths of screws, specifically translaminar screws, the implantable device 22 of the system 20 allows a gradient of fixation strength across the device 22. The top level of the device 22 may allow some degree of movement, thereby creating a dynamic stabilization scheme. The bottom level of the device 22 may be more rigidly fixed as a result of the longer pair of translaminar screws 60 being used, thereby forming a tighter, more secure connection with the lower vertebra. In contrast, the shorter pair of screws 50 applied at the top level may sufficiently prevent the spacer body 22 from moving out of position, but may be sufficiently loose so as to allow a small amount of micromotion between the spacer body 22 and spinous process or vertebra, so as not to promote fusion, or at least cause fusion to occur more slowly.

When system 20 is configured to allow some dynamic motion, it is contemplated that the apertures 42 of the implantable device 22, particularly at the level where the motion is to occur, would be configured to accommodate the movement of the screws 50. For instance, the apertures 42 may be elongated slots or other shapes to allow the heads of the screws to "rock" back and forth during motion. Further, in some embodiments, the system 20 can include only a single pair of fixation elements. For example, two bone screws 60 may be used to secure either the top or bottom level of the adjacent vertebrae. Thus, the spacer body 22 may be secured to one vertebra and not the other adjacent vertebra.

While FIGS. 3 and 4A-4C illustrate a system 20 in which a pair of shorter screws 50 is used with the top level of the implantable device 22, it is understood that the same system 20 could easily accommodate the use of shorter screws 50 at the bottom level, while the longer screws 60 could be used at the top level. In other words, the set of screws 50, 60 shown could be reversed, so that each set 50, 60 could equally be used at either level of the device 22. In addition, the screws 50, 60 may differ from one another in other manners, such as diameter, thread pitch, etc. as well as length. Accordingly, a user may customize the system 20 in a number of ways depending on the particular need of the patient.

Figure 5:
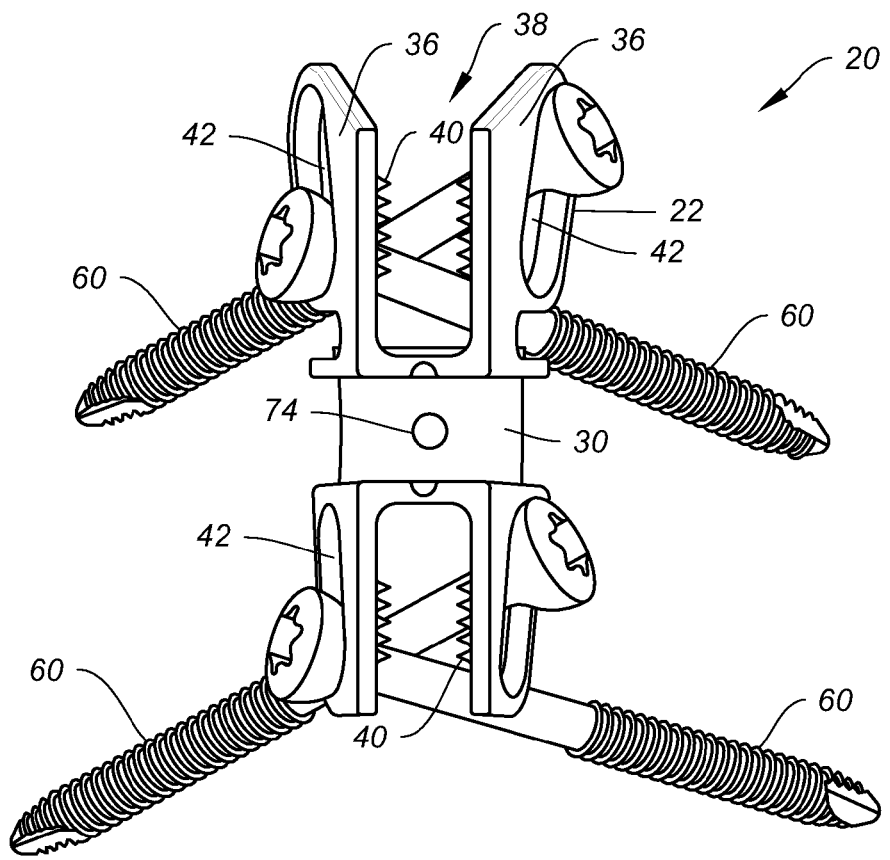
FIG. 5 illustrates a front perspective view of another embodiment of a translaminar interspinous stabilization system of the present disclosure.

FIG. 5 illustrates a system 20 in which the same or very similar pairs of screws 60 are used with the implantable device 22 at the top and bottom levels. That is, the screws 60 used at both levels have the same relative strength. In this particular configuration, the system 20 may serve to promote fusion of the relevant vertebrae. It is envisioned that a tight, secure connection between the spacer body 22 and adjacent vertebrae will limit movement at the selected vertebral level, thereby promoting fusion at that level.

In some embodiments, a stiffening plug or insert 70 may be used to provide additional stiffness, particularly at the midsection 30. FIGS. 6A-6B, 7A-7C and 8 illustrate the system 20 and implantable device 22 of FIG. 5 whereby a stiffening insert 70 is placed inside the U-shaped midsection 30 of the spacer body 22. The stiffening insert 70 may be formed as a material folded onto itself, as shown in FIGS. 6A-6B, 7B, and 7C. Alternatively, the stiffening insert 70 may be formed as a unitary body.

Figure 6A:
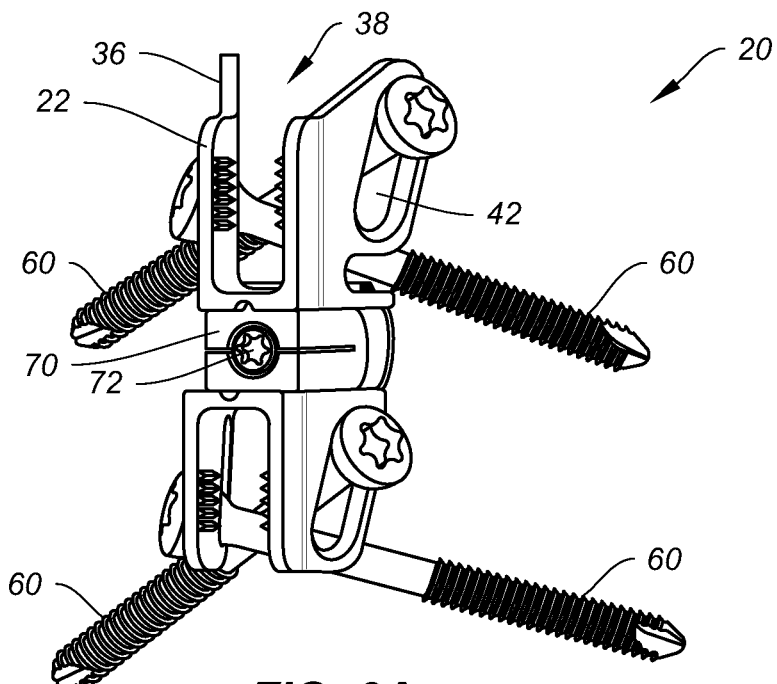
FIG. 6A illustrates a perspective view of yet another embodiment of a translaminar interspinous stabilization system of the present disclosure.
Figure 6B:
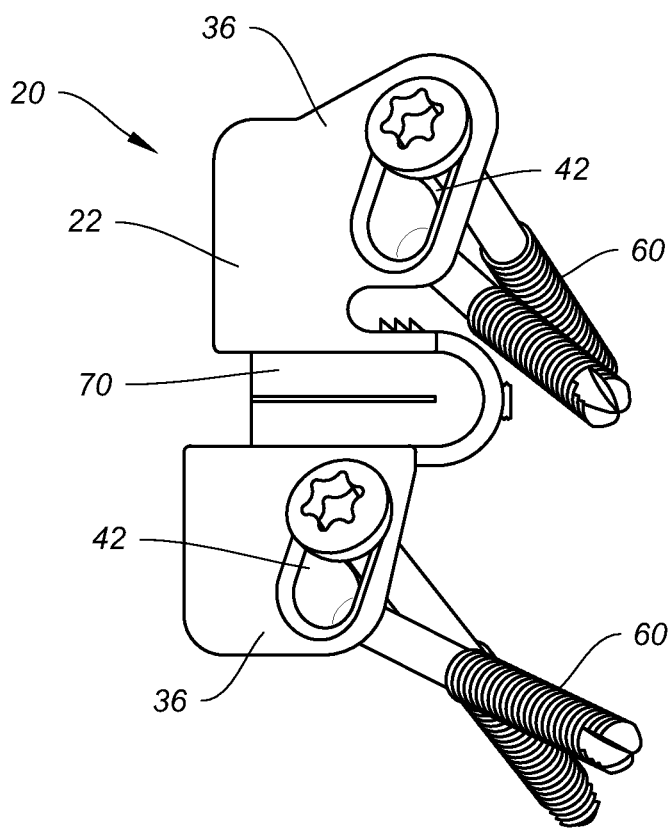
FIG. 6B illustrates a side view of the system of FIG. 6A.
Figure 7A:
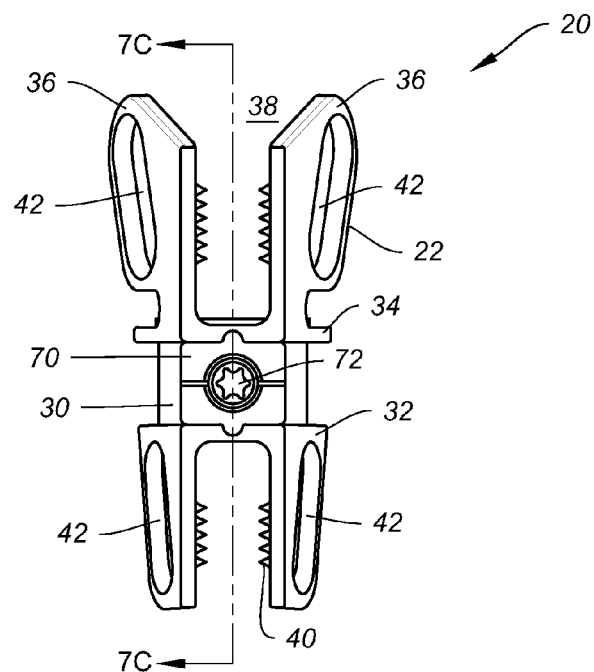
FIG. 7A illustrates a front perspective view of the interspinous stabilization device and spacer of FIG. 6A.
Figures 7B, 7C:
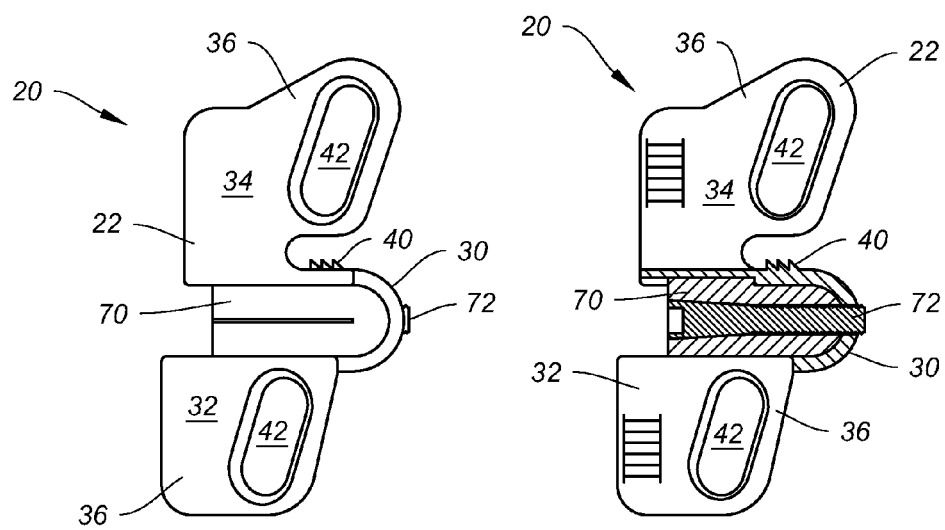
FIG. 7B illustrates a side view of the interspinous stabilization device and spacer of FIG. 7A.
FIG. 7C illustrates a cross-sectional view of the interspinous stabilization device and spacer of FIG. 7A along lines 7C-7C.
Figure 8:
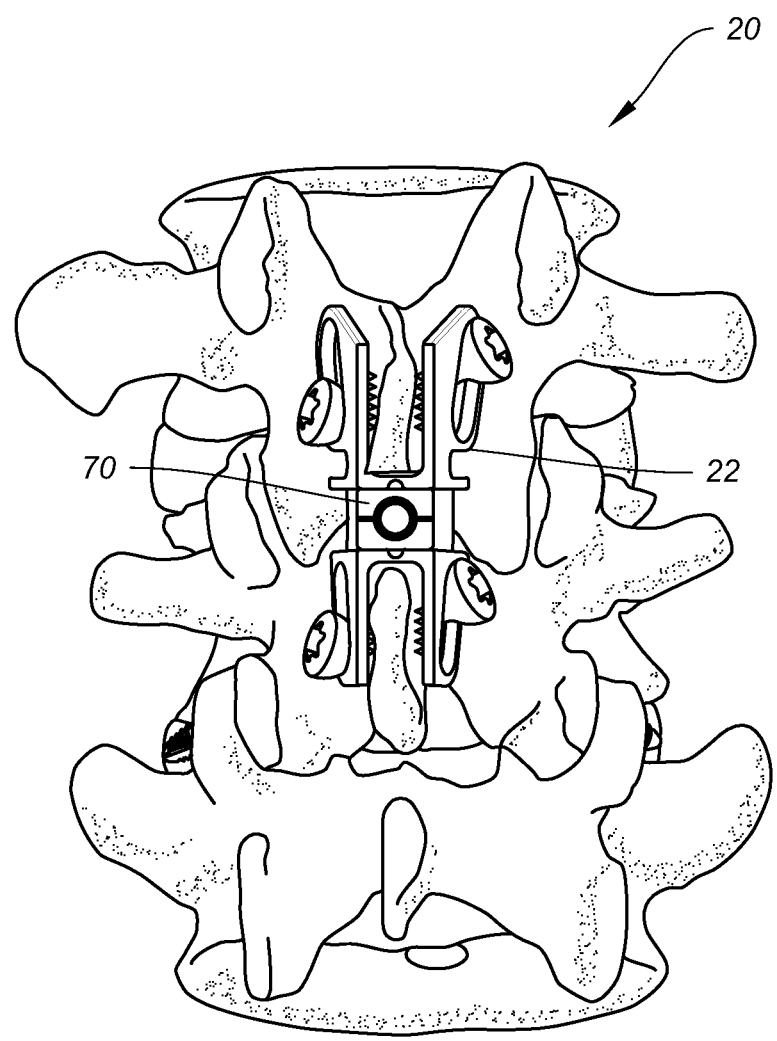
FIG. 8 illustrates a perspective view of the implanted system of FIG. 7A in situ.

As shown, the insert 70 may be configured with an opening to receive a fixation or attachment element 72, such as a screw, plug, rivet, spike, etc. The attachment element 72 may be configured for insertion through a hole 74 on the spacer body 22, as seen in FIG. 5. In one example, the hole 74 may be threaded and the attachment element 72 may include threads at its terminal end, as shown in more detail in FIG. 7C. The attachment element 72 may include a tool-engaging opening to facilitate insertion with a tool (not shown), as illustrated in FIGS. 6A, 7A and 7C. In addition, as shown in FIGS. 6A and 7A, the stiffening insert 70 may be configured with a surface feature such as a protrusion or geometric shape that complements a groove or slot within the spacer body 22 for receiving the stiffening insert 70. In one embodiment, a dovetail connection or other shape-fitting connection, for example, could be provided between the stiffening insert 70 and the spacer body 22.

To further enhance the ability of the implantable device 22 to be secured to the surrounding bone and soft tissue, the implantable device 22 may include a number of surface modifications. For example, the spacer body 22 may include surface alterations that may facilitate tissue attachment, bonding, or fixation. These surface alterations may include teeth, barbs, beads, surface roughening, or the addition of bioactive agents to one or more sections of the device 22. For example, the device 22 may include one or more teeth or barbs 40 for securing the device 22 to bone and/or soft tissue. As shown, the teeth 40 may be located on the spacer body 22, such as on an outer surface of the inferior section 32 and/or superior section 34. Alternatively, or in addition, the barbs 40 may be located on an inner surface of the lateral walls 36. The barbs 40 may help the spacer body 22 securely engage connective tissue or a bony surface of a vertebra, such as the spinous process of the vertebra.

Additionally, the implantable device 22 may also include roughened or porous surfaces, for example, to promote bony ingrowth. The roughened or porous surfaces may enhance attachment between implant surfaces and bone. In addition, some porous surfaces may facilitate tissue ingrowth to form a biological bond between sections of the device 22 and the surrounding bone and/or soft tissue. Roughened or porous surfaces may be included on any portion of the device 22.

The surface of the device 22 may also include biologically active agents. These agents may include osteogenic factors to further facilitate bonding between components of the device 22 and the surrounding bone and/or soft tissue. Further, the device 22 may include therapeutic agents, such as antibiotics, steroids, anti-thrombotic agents, anti-inflammatory drugs, and/or analgesic agents. In one embodiment, the biologically active agent may be contained in a coating on the device. Alternatively, or in addition, the device may be porous, and the biologically active agent may be contained in the pores of the device. The biologically active agent may be, for example, bone morphogenic protein (BMP) for modulating cartilage or bone growth.

A number of biocompatible materials are suitable for forming the spacer body 22 of the present disclosure. In one embodiment, the spacer body 22 may be formed from a medical grade metal, such as titanium or a titanium alloy. The spacer body 22 may also be formed from a variety of other materials, such as stainless steel, cobalt chrome, ceramics, and/or polymeric materials, such as ultra-high molecular-weight polyethylene (UHMWPE) and polyetheretherketone (PEEK), either alone or in combination with other suitable materials.

Although the implantable device 22 is described and shown with superior and inferior lateral walls 36, the device 22 can also comprise a U-shaped implant with a single pair of lateral walls 36. Such devices may be used at the L5-S1 vertebral level. For example, the device 22 may include a single pair of lateral walls 36 configured to engage the spinous process and lamina of the L5 vertebra. Further, the device 22 may include a mechanism for securing the inferior section 32 to the sacrum. As noted above, the superior lateral walls can be secured to the L5 spinous process with translaminar screws 60, thereby limiting movement at the L5-S1 level and promoting fusion at that level.

Figure 9A:
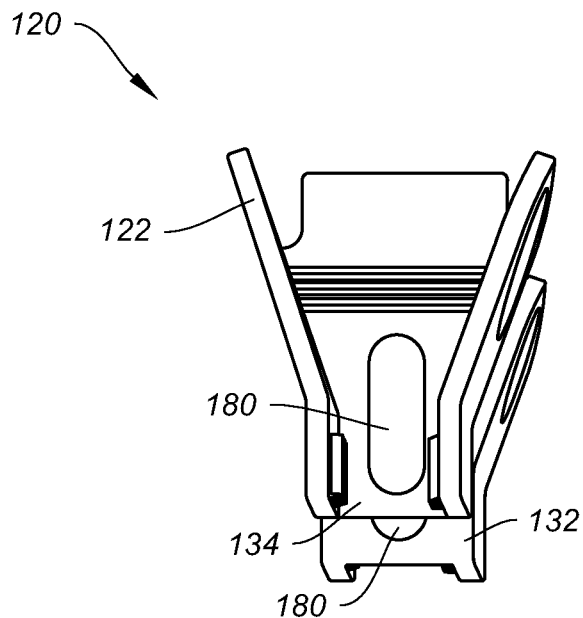
FIG. 9A illustrates a top-down view of another embodiment of an implantable device of the present invention.
Figure 9B:
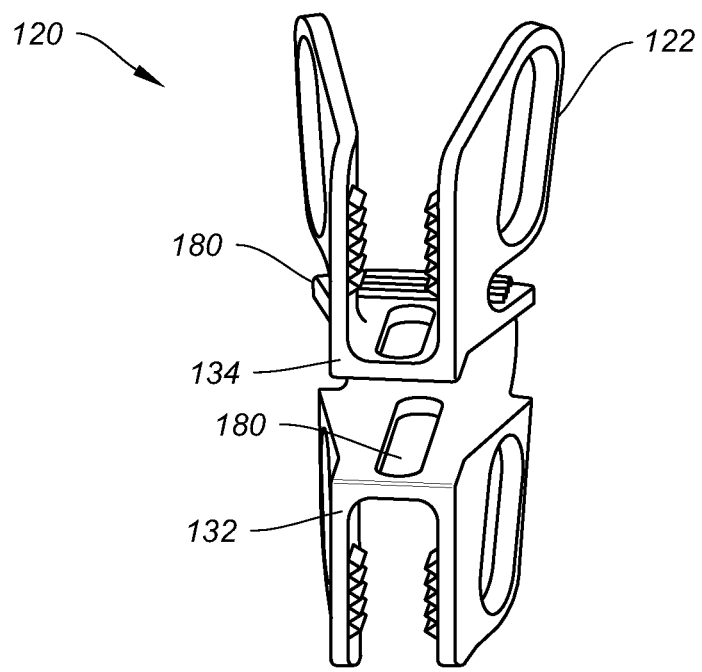
FIG. 9B illustrates a perspective view of the implantable device of FIG. 9A.

FIGS. 9A-9B and 10A-10B illustrate additional exemplary embodiments of implantable devices of the present disclosure. FIGS. 9A and 9B illustrate one embodiment of an implantable device 122 for use in a translaminar interspinous stabilization system 120 similar to the system 20 previously described. The implantable device 122 shown in FIGS. 9A and 9B shares similar features to the previously disclosed implantable device 22, whereby these like features or structures are indicated by the same reference numerals used for implantable device 22, following the prefix "1". However, in addition to having all of the features of implantable device 22, implantable device 122 of FIGS. 9A and 9B is provided with additional portals or openings 180 for receiving or inserting a fusion promoting material, as well as for allowing bony ingrowth. The openings 180 may be located on the inferior and superior sections 132, 134 and may be configured as one or more circles, slots, squares, rectangles, etc. For example, FIGS. 9A and 9B illustrate an embodiment in which an opening 180 is provided on each of the inferior and superior sections 132, 134 of the implantable device 122.

Figure 10A:
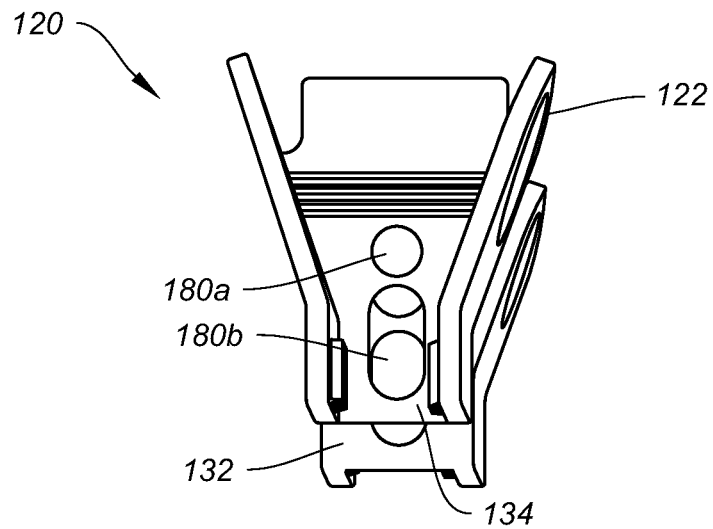
FIG. 10A illustrates a top-down view of still another embodiment of an implantable device of the present invention.
Figure 10B:
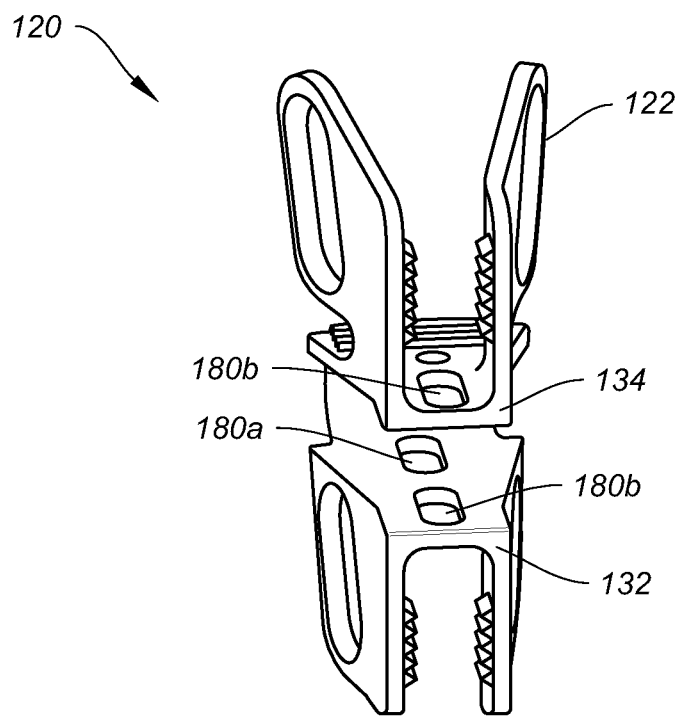
FIG. 10B illustrates a perspective view of the implantable device of FIG. 10A.

FIGS. 10A and 10B, on the other hand, illustrate an embodiment in which more than one opening 180a, 180b is provided on each of the inferior and superior sections 132, 134 of the implantable device 122. As further shown in FIG. 10A, the size and shape of the openings 180a, 180b may differ from section to section. In one embodiment, opening 180a may be smaller than opening 180b. The openings 180a, 180b may allow access to receive a fusion promoting material, such as a bone substitute material, an allograft or autograft material, or other graft material effective to enhance bone growth and fusion. Additionally, the openings 180 may serve as portals for bony ingrowth.

As shown and described, the present disclosure provides interspinous stabilization systems that can be configured to provide either dynamic or rigid stability to the affected vertebral segment of the spinal column. For instance, the system may allow dynamic stability for controlled motion of the adjacent vertebrae being affected. One contemplated manner of achieving this is by adjusting or varying the type of translaminar screw being used. However, as further shown and described, the same system may also be easily converted or adapted to allow for rigid, fusion-promoting securement, if so desired or needed. This can be achieved through the manner of fixation, such as with the type of translaminar screw being used or the number of screws being used. Another manner of promoting fusion with the same system is with the use of a stiffening insert or plug, or fusion promoting material such as bone graft material or other bone growth inducing material.

Figure 11A:
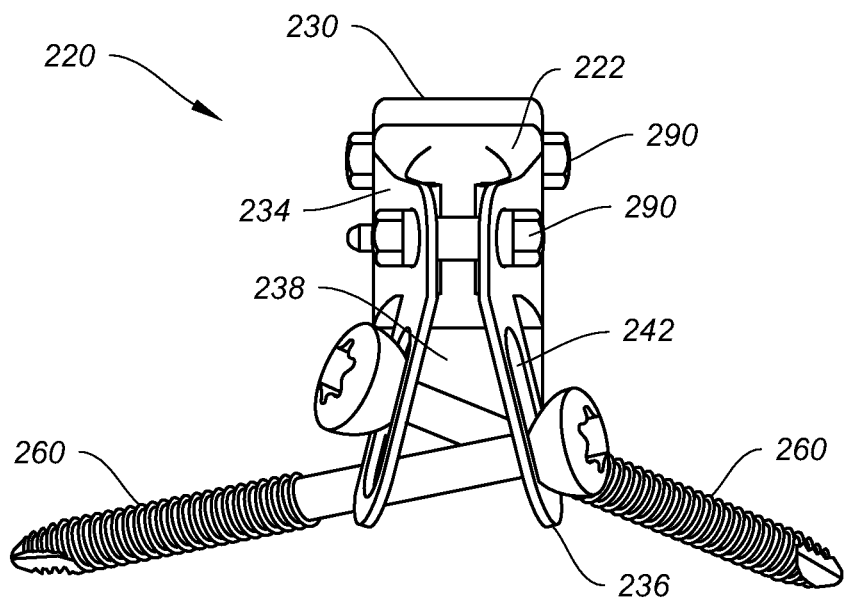
FIG. 11A illustrates a top-down view of still another embodiment of a translaminar interspinous stabilization system of the present disclosure.
Figure 11B:
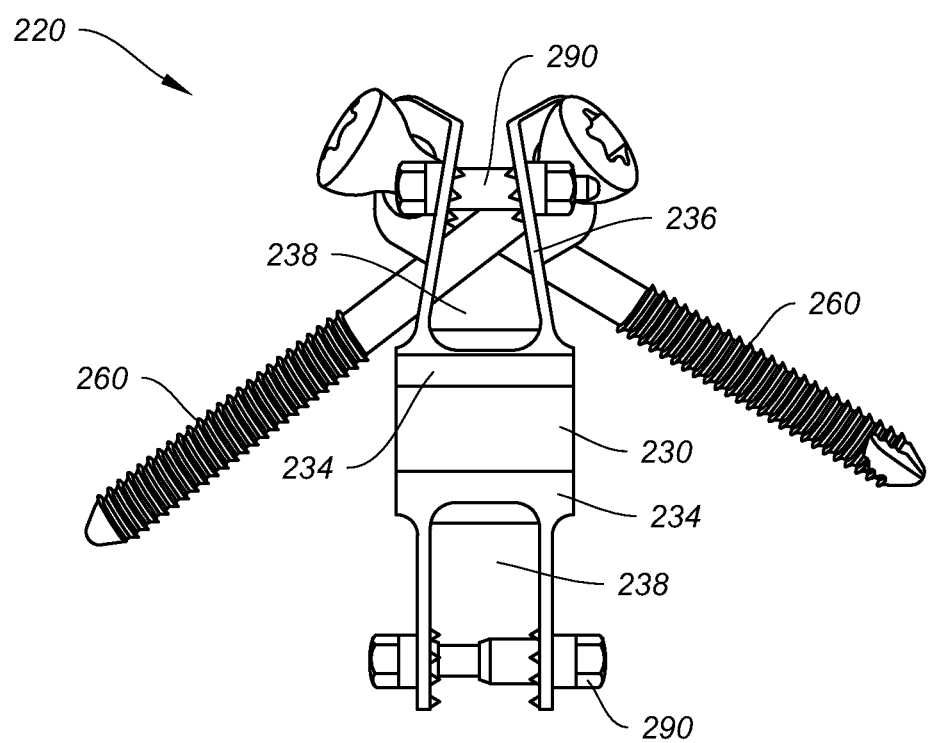
FIG. 11B illustrates a perspective view of the system of FIG. 11A.
Figure 12:
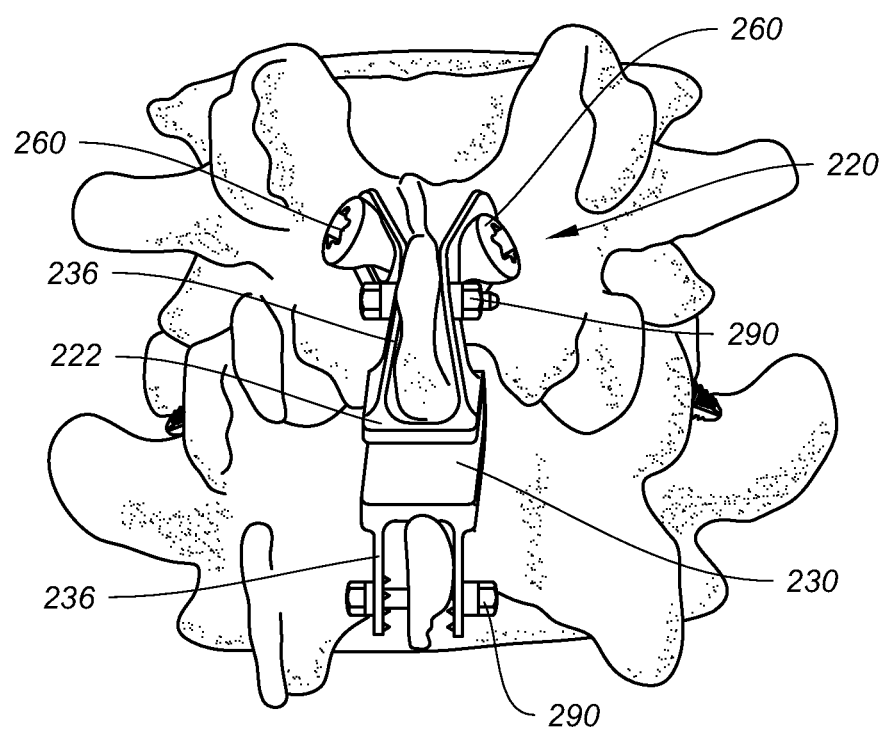
FIG. 12 illustrates a perspective view of the implanted system of FIG. 11A in situ.

FIGS. 11A, 11B and 12 describe still another exemplary embodiment of a translaminar interspinous stabilization system 220 of the present disclosure. FIGS. 11A and 11B illustrate one embodiment of an implantable device 222 for use in a translaminar interspinous stabilization system 220 similar to the system 20 previously described. The implantable device 222 shown in FIGS. 11A and 11B shares similar features to the previously disclosed implantable device 22, whereby these like features or structures are indicated by the same reference numerals used for implantable device 22, following the prefix "2". However, in addition to having all of the features of implantable device 22, implantable device 222 of FIGS. 11A and 11B may further contain openings for receiving a fixation element such as a rivet, bolt and nut, or other similar fastener 290. The location of the opening for the fastener 290, and the fastener itself, may be configured so as to allow fixation through a spinous process, thereby securing the lateral walls 236 of the implantable device 222 to the spinous process. As shown, the device 222 may be configured to receive the fastener 290 at either of the top or bottom levels. In one embodiment, the fastener 290, as well as the manner of receiving the fastener 290 within the implantable device 222 and its assembly, may be similar in respect to the one disclosed in U.S. Pat. No. 7,922,750 entitled "Interlaminar-Interspinous Vertebral Stabilization System."

As shown in FIGS. 11A and 11B, the system 220 may comprise an implantable device 222 that can accommodate a fastener 290 at both the top and bottom levels through the upper and lower lateral walls 236. In addition, the implantable device 222 may also allow for a pair of translaminar screws 260 to be used at the top level, as shown in FIG. 12. It is, of course, understood that the system 220 may easily be configured to allow translaminar screws 260 to be used at both the top and bottom levels, as previously described and shown, for even greater anchorage. By securely attaching the implantable device 222 to the vertebra, the system 220 of the present disclosure provides a fusion-promoting system for vertebral stabilization.

The systems 20, 120, 220 of the present disclosure allow the user great flexibility in adapting the systems to the current needs of the patient. As already mentioned, the systems can provide the option of either dynamic or rigid stability. The systems can also be adapted for different uses over time. For example, a clinician may initially use one of the systems for dynamic stability, and then over time as the patient's needs changes, the clinician can modify the existing implanted system to allow for more rigid stability, such as by inserting a stiffening plug into the device, or inserting some bone growth promoting material, or even inserting translaminar screws or a fastener to the implantable device where one was not already present. Thus, the dynamic stability of the initial system can be converted into a rigidly stable system without great effort.

It is contemplated that multiple systems 20, 120, 220 of the present disclosure may be used together for multi-level vertebral stabilization. These systems may be identical, or they may be different, and can be used at the same time or over time with the patient's changing needs. For example, system 20 may be used at one level while system 220 is used at a different level, either at the same time or at different times such as where system 220 is implanted after system 20 has already been implanted. Likewise, each of these systems 20, 120, 220 may be used with other implantable interspinous devices, such as those currently available and previously mentioned, thereby allowing ultimate flexibility and variability in terms of the combination of devices that can be used to address the patient's particular needs.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A translaminar, interspinous stabilization system comprising:
    an implantable device for placement between two adjacent vertebrae, the device comprising an inferior section, a superior section, a flexible midsection extending therebetween, and two pairs of lateral plates for engaging a laminar surface of the two adjacent vertebrae, each of the lateral plates including an aperture for receiving a bone screw therethrough; and
    at least one first bone screw for placement through the aperture of a lateral plate of one of the pairs of lateral plates, and at least one second bone screw for placement through the aperture of a lateral plate of the other of the pairs of lateral plates, the first and second bone screws for securing the device to the laminar surface of the two adjacent vertebrae,
    wherein the first bone screw allows for dynamic stabilization and the second bone screw differs from the first bone screw and allows for rigid stabilization.

2. The system of claim 1, wherein the inferior section, superior section and flexible midsection together form a U-shaped body.

3. The system of claim 2, wherein the flexible midsection is configured for interlaminar placement between the adjacent vertebrae.

4. The system of claim 1, wherein the flexible midsection is compressible and extendable.

5. The system of claim 1, wherein the pairs of lateral plates extend outwardly from the superior and inferior sections.

6. The system of claim 5, wherein at least one pair of lateral plates includes a further opening for receiving a fastener therethrough, the opening being configured to allow the fastener to secure the lateral plates against a spinous process.

7. The system of claim 1, wherein the pairs of lateral plates are contoured to match the anatomic shape of the laminar surface.

8. The system of claim 1, wherein the aperture of the lateral plates comprises an elongated slot.

9. The system of claim 1, wherein the length of the first bone screw is different than the length of the second bone screw.

10. The system of claim 9, wherein the length of the first bone screw is shorter than the length of the second bone screw.

11. The system of claim 1, further including a rigid insert for placement within the flexible midsection.

12. The system of claim 1, wherein at least one of the inferior and superior sections includes an opening for insertion of material or for accommodating bone growth therethrough.

13. The system of claim 12, further including a fusion promoting material for placement within the flexible midsection through the opening.

14. The system of claim 13, wherein the fusion promoting material comprises allograft, autograft, or bone substitute material.

* * * * *